United States Patent [19]

Bernhart et al.

[11] Patent Number: 4,721,710
[45] Date of Patent: Jan. 26, 1988

[54] DERIVATIVES OF PIPERIDINEDIONE FOR PROTECTING THE MYOCARDIUM PRESENTING AN ANTI-ARRYTHMIC ACTIVITY, AND PHARMACEUTICAL COMPOSITIONS

[75] Inventors: Claude Bernhart, Saint Gely du Fesc; Werner Cautreels, Castelnau le Lez; Patrick Gautier, Cournonterral, all of France

[73] Assignee: Sanofi

[21] Appl. No.: 838,255

[22] Filed: Mar. 10, 1986

Related U.S. Application Data

[63] Continuation of Ser. No. 545,507, Oct. 26, 1983, abandoned.

[30] Foreign Application Priority Data

Nov. 8, 1982 [FR] France ............................... 82 18706

[51] Int. Cl.⁴ .................. A61K 31/45; A61K 31/538; C07D 401/04; C07D 413/04
[52] U.S. Cl. .................................... 514/234; 514/316; 514/318; 544/130; 546/16; 546/112; 546/142; 546/187; 546/193
[58] Field of Search .................. 544/130; 546/16, 112, 546/142, 187, 193; 514/234, 316, 318

[56] References Cited

U.S. PATENT DOCUMENTS 2,664,424 12/1953 Hoffmann et al. .................. 546/193

Primary Examiner—Robert W. Ramsuer

[57] ABSTRACT

The present invention relates to derivatives of piperidinedione of formula:

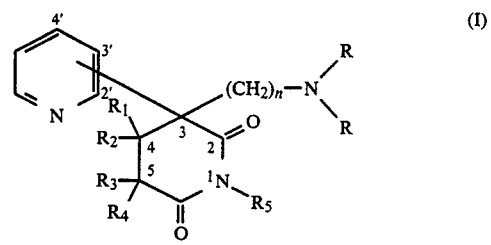

in which R is alkyl or forms with N a possibly substituted morpholino or piperidino group, n=2 or 3, $R_1$, $R_2$, $R_3$ and $R_4$ represent H or lower alkyl; $R_3$ and $R_4$ taken together may represent $(CH_2)_m$ where m=4 or 5 and $R_2$ and $R_3$ taken together may represent $(CH_2)_p$ where p=3 or 4 and in this case $R_1$ and $R_4$=H, $R_5$ is H or alkyl. It also relates to a process for manufacturing the product of formula (I) and to the drugs containing a product of formula (I).

9 Claims, No Drawings

DERIVATIVES OF PIPERIDINEDIONE FOR PROTECTING THE MYOCARDIUM PRESENTING AN ANTI-ARRYTHMIC ACTIVITY, AND PHARMACEUTICAL COMPOSITIONS

This application is a continuation of application Ser. No. 545,507, filed Oct. 26, 1983, now abandoned.

The present invention relates as new industrial products to derivatives of 2,6-piperidinedione, as well as to the methods for preparing them and to the application thereof in therapeutics.

The novel compounds according to the invention respond to general formula:

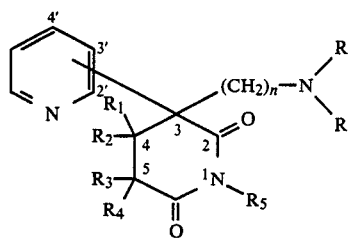

in which:
R represents a straight or branched alkyl group having from 2 to 5 atoms of carbon, or the group

represents a morpholino or piperidino group possibly substituted by 1 to 4 methyl groups;
n=2 or 3;
$R_1$ and $R_2$ considered independently represent an atom of hydrogen or a lower alkyl group,
$R_3$ and $R_4$ considered independently represent hydrogen or a lower alkyl group or
$R_3$ and $R_4$ taken together represent a $(CH_2)_m$ group where m=4 or 5
or $R_2$ and $R_3$ taken represent a $(CH_2)_p$ group where p=3 or 4 and in this case $R_1$ and $R_4$ are hydrogen,
$R_5$ designates hydrogen or a lower alkyl group,
finally piperidinedione substitutes the pyridyl group in 2', 3' or 4' position.

In the present specification, lower alkyl group is understood to mean a straight or branched alkyl group having from 1 to 4 carbon atoms.

Compounds (I) furnish with the organic or inorganic acids soluble salts. These salts with pharmaceutically acceptable acids form an integral part of the invention.

Compounds (I) always possess an asymmetrical carbon atom, namely atom 3 of the piperidinedione cycle. If substituents $R_1$ and $R_2$ on the one hand or $R_3$ and $R_4$ on the other hand are different from one another, there exist in the molecule one or two other asymmetrical carbon atoms. Consequently, compounds (I) may exist in the form of diastereoisomers and optical isomers. All these isomers as well as mixtures thereof form an integral part of the invention.

The compounds according to the invention are obtained from a pyridylacetonitrile in accordance with one of the two methods of preparation indicated hereinafter:

Method A

This method is represented by the reaction diagram hereinbelow:

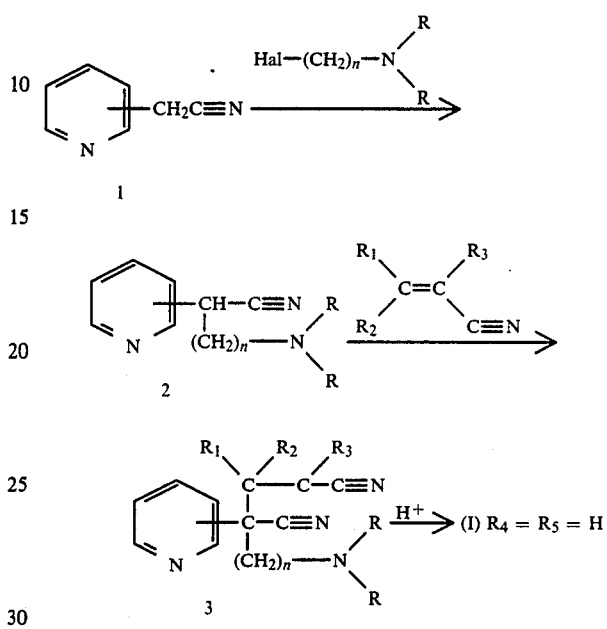

Pyridylacetonitrile 1 is firstly subjected to a reaction of alkylation by a compound:

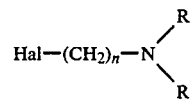

(Hal representing a halogen) in the presence of an organic or inorganic base to lead to compound 2.

The latter is again substituted by action of an α-unsaturated nitrile

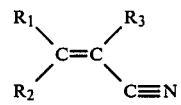

to lead to compound 3. Operation is most often carried out within an inert solvent, such as tetrahydrofuran, in the presence of a quaternary ammonium hydroxide, such as benzyltrimethylammonium hydroxide, at a temperature of between 0° and 30° C.

The reaction may also be carried out in the presence of sodium amide within the liquid ammonia at a temperature of between −30° and −40° C. Compound 3 is cyclized into compound (1), $R_5$=H, by heating in an acid medium. Either hydrochloric acid in acetic acid medium, concentrated sulfuric acid, or polyphosphoric acid at a temperature of between 100° and 150° C. is used.

Method B

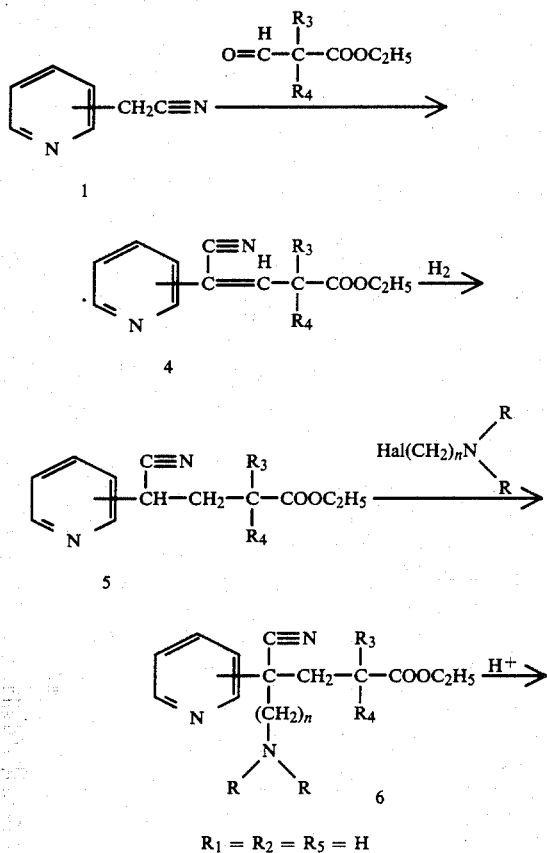

$R_1 = R_2 = R_5 = H$

On the pyridylacetonitrile 1 there is reacted a carbonyl derivative

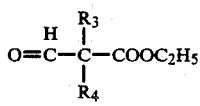

which leads to the unsaturated ester nitrile 4.

Operation is carried out in an inert solvent, such as benzene, most often at boiling temperature of the solvent, adding as catalyst either paratoluenesulfonic acid or piperidine and acetic acid. Derivative 4 is converted into corresponding saturated derivative by catalytic reduction. Operation is carried out in solution in ethanol in the presence of a catalyst of hydrogenation such as palladium on charcoal at ambient temperature under a pressure of 1 atmosphere.

Compound 5 is substituted on the carbon in α of the nitrile by action of a compound:

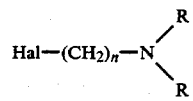

in the presence of a sodation agent, such as sodium hydride, within a solvent such as dimethylformamide. Most often, operation is carried out at a temperature of between 20° and 50° C.

Finally, compound 5 is cyclized into product (I) $R_5=H$ by heating to a temperature included between 80° and 120° C. with concentrated sulfuric acid.

Method C

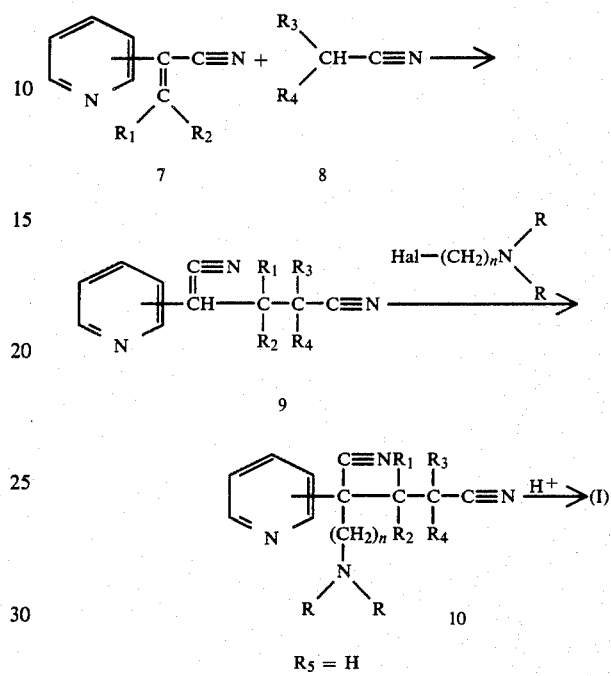

$R_5 = H$

Condensation of nitrile 8 on the unsaturated nitrile 7 leads to a dinitrile 9. Condensation is effected in the presence of lithium diisopropylamide (prepared in situ by action of diisopropylamine on a solution of butylithium) at low temperature and in solution in a solvent such as tetrahydrofuran.

The dinitrile 9 is then substituted by action of a halogen derivative

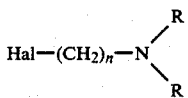

to obtain the dinitrile 10. Operation is carried out in the presence of a sodation agent such as sodium hydride within an inert solvent such as dimethylformamide. Finally, the dinitrile 10 is cyclized by action of a concentrated inorganic acid such as sulfuric acid at a temperature of between 80° and 120° C.

Method D

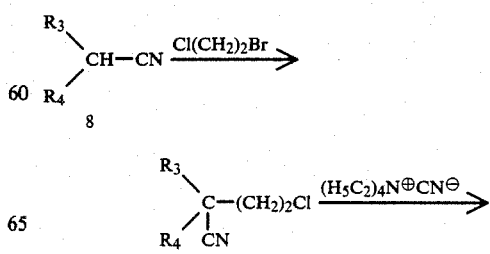

-continued

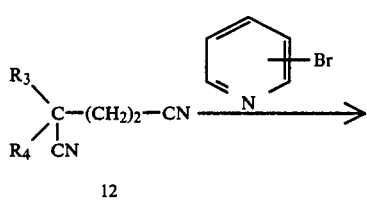

12

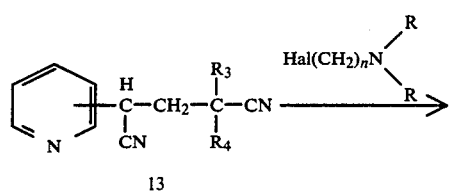

13

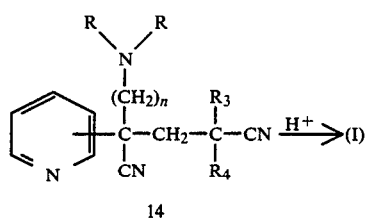

14

$R_1 = R_2 = R_5 = H$

The nitrile 8 is substituted by 1-chloro 2-bromo ethane to obtain the chlorinated nitrile 11. The substitution preferably takes place in the presence of lithium diethylamide (prepared in situ by action of diethyl amine or butyllithium) at ambient temperature in an inert solvent such as ether or tetrahydrofuran.

By action on 11 of a cyanide and preferably tetraethylammonium cyanide, the dinitrile 12 is obtained. Operation is carried out within a solvent of the 2 reagents such as acetonitrile at a temperature of 40° to 60° C.

The dinitrile 12 is substituted by a bromopyridine to obtain the dinitrile 13. Operation is carried out in the presence of lithium diisopropylamide within a solvent such as tetrahydrofuran and a temperature of −10° to −20° C. The dintrile 13 is substituted a second time by a halogen derivative

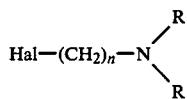

by operating in identical manner to that employed for the dinitrile 10 in method C.

Finally, by acid hydrolysis as indicated for the dinitrile 10, in method C, compound (I) is obtained, with $R_1 = R_2 = R_5 = H$.

Compounds (I) where $R_5$ is alkyl are obtained from the compounds where $R_5$ is hydrogen and obtained by one of methods A or B by alkylation with nitrogen in accordance with a known method, for example by action of an alkyl halide on the sodium derivative obtained by action of sodium hydride on compound (I), $R_5 = H$ within a solvent such as dimethylformamide.

The salts of compounds (I) are obtained by the conventional method of salification.

Finally, when $R_1$ and $R_2$ on the one hand or $R_3$ and $R_4$ on the other hand are different, products (I) exist in the form of diastereoisomers. Methods A and B lead to a mixture of these diastereoisomers which may be separated by the conventional methods and in particular by chromatography.

On each of the diastereoisomers, a study of nuclear magnetic resonance has made it possible to determine in spatial configuration of these stereoisomers.

The following examples, which are in no way limiting, are given by way of illustration for the preparation of the compounds according to the invention.

In the following examples, for designating the diastereoisomers, the nomenclature of the IUPAC—Section E (recommendation of 1974) and in particular rule E-5.3. will be used.

EXAMPLE 1

5(e)-methyl 3(e)-(2-diisopropylamino ethyl) 3(a)-(2-pyridyl 2,6-piperidinedione dihydrochloride (SR 40976)

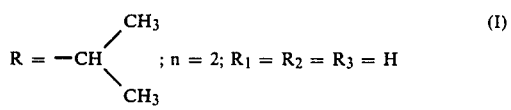

$R_4$ = equatorial —$CH_3$; $R_5$ = H (a) 4-diisopropylamino 2-(2-pyridyl) butane nitrile 80 g of 2-pyridyl acetonitrile, 8.8 g of 1-chloro 2-diisopropylamino ethane and 2.7 g of benzyltriethylammonium chloride are mixed. Whilst maintaining the temperature below 35° C., 350 ml of a 50% aqueous solution of sodium hydroxide are added little by little.

The mixture is heated to 35° C. for 5 hours. After cooling, water is added and the mixture is extracted with ether. The organic phase is separated, dried over sodium sulfate then the solvent is evaporated to dryness.

By distillation of the residue, a yellow liquid is obtained (94 g); b.p./0.6 mm Hg: 132°–134° C.

(b) 2-(2-diisopropylamino ethyl) 4-methyl 2-(2-pyridyl) pentane dinitrile

To a solution of 17.3 g of the nitrile obtained hereinabove in 70 ml of tetrahydrofuran are added 3.2 ml of a 40% solution of benzyltrimethylammonium hydroxide in methanol. The solution of 5.2 g of methacrylonitrile in 35 ml of tetrahydrofuran is added drop by drop and the mixture is then left for 1 hour with stirring.

The solvent is evaporated to dryness and the residue is taken up in water and ether. The ethereal phase is separated and the aqueous phase is re-extracted with ether. The ethereal extracts are collected, washed with water and dried over sodium sulfate. The solvent is evaporated to dryness.

An orange-yellow liquid is obtained (22.7 g) used as such for the continuation of the operation.

(c) SR 40976

The mixture of 22.7 g of the dinitrile obtained previously, 136 ml of hydrochloric acid (d=1.19) and 136 ml of acetic acid is heated to reflux for 2 hours.

The mixture is evaporated to dryness in vacuo and the residue is taken up in a little water. A saturated solution of sodium bicarbonate is added and the mixture is extracted 3 times with chloroform. The organic extracts are collected, dried over sodium sulfate and the solvent is evaporated to dryness.

16 g of crude product constituted by the mixture of the two diastereoisomers are obtained and are chromatographed over a column of alumina. By eluting with an ethyl acetate-pentane (30-70) vol/vol mixture, one of the pure diastereoisomers is firstly obtained (5.35 g).

A study of the NMR spectrum of the product shows that, in this diastereoisomer, the methyl in 5 position and the (2-diisopropylamino ethyl) group in 3 position are equatorial, whilst the 2-pyridyl group is axial.

Dihydrochloride 5.02 g of the pure diastereoisomer hereinabove are dissolved in 50 ml of absolute ethanol and 3.07 g of hydrochloric acid (d=1.19) dissolved in 50 ml of absolute ethanol are added. The solvent is evaporated and the residue is taken up in acetone. The dihydrochloride crystallizes in the form of colourless crystals, is drained and washed with a little acetone. Weight: 6.26 g; m.p. 157°-160° C. The dihydrochloride crystallizes with 1 molecule of water.

EXAMPLE 2

3-(2-diisopropylamino ethyl) 3-(2-pyridyl) 2,6-piperidinedione (SR 41299)

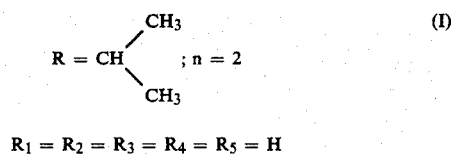

$R_1 = R_2 = R_3 = R_4 = R_5 = H$ (a) 2-diisopropylamino 2-(2-pyridyl) pentane dinitrile Operation is carried out as in Example 1(b), from the nitrile of Example 1(a), but replacing the methacrylonitrile by acrylonitrile. (b) SR 42199

11.6 g of the compound obtained hereinabove and 110 g of polyphosphoric acid are heated to 115° C. for an hour and a half. After cooling, the reaction medium is dissolved in water and is rendered alkaline with potassium carbonate. The mixture is extracted with ethyl acetate, dried over sodium sulfate then the solvent is evaporated to dryness.

The residue is chromatographed over a column of alumina, eluting with an ethyl acetate-pentane, firstly 50-50 vol/vol, then 75-25 vol/vol, mixture. In this way, an oil is obtained which crystallize slowly. It is recrystallized in isopropyl ether and colourless crystals are obtained (5.25 g). m.p. 96°-97° C.

EXAMPLE 3

5(e)-isopropyl 3(e)-(2-diisopropylamino ethyl) 3(a)-2-pyridyl) 2,6-piperidinedione (SR 41411)

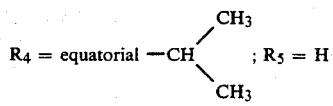

(a) 2-(2-diisopropylamino ethyl) 4-isopropyl 2-(2-pyridyl) pentane dinitrile

Operation is carried out as in Example 1(b), from the nitrile of Example 1(a), but replacing the methacrylonitrile by an equivalent quantity of 2-isopropyl acrylonitrile.

(b) SR 41411

17 g of the dinitrile prepared hereinabove are dissolved in 100 ml of concentrated sulfuric acid (d: 1.83), then heated to 100°-110° C. for 1 hour. The reaction mixture is poured over ice and the solution is rendered alkaline by a 40% solution of sodium hydroxide. The mixture is extracted with ethyl acetate and the organic solution is dried over sodium sulfate.

The solvent is evaporated to dryness and the residue is chromatographed over a column of alumina. By eluting with the ethyl acetate-pentane (20/80) vol/vol mixture, 5.3 g of pure diastereoisomer are firstly obtained, then 3.3 g of a mixture of the two diastereoisomers.

The pure diastereoisomer is recrystallized in isopropyl ether; m.p. 123°-125° C.

By operating as in Example 3, but by varying the acrylonitrile used in step (a), the following is obtained:
with 2-isobutyl acrylonitrile:
5(e)-isobutyl 3(e)-(2-diisopropylamino ethyl) 3(a)-(2-pyridyl) 2,6-piperidinedione (SR 41463), m.p. 112°-114° C. (hexane),
with 2-ethyl acrylonitrile:
5(e)-ethyl 3(e)-(2-diisopropylamino ethyl) 3(a)-(2-pyridyl) 2,6-piperidinedione (SR 41575),

EXAMPLE 4

5-tertiobutyl 3-(2-diisopropylamino ethyl) 3-(2-pyridyl) 2,6-piperidinedione (a) 2-(2-diisopropylamino ethyl) 4-tertiobutyl 2-(2-pyridyl) pentane-dinitrile Operation is carried out as in Example 1(b), replacing the methacrylonitrile by 2-tertiobutyl acrylonitrile in an equivalent quantity.

(b) Cyclization

Operation is carried out as in Example 3(b) from the product obtained hereinbefore.

The crude product of reaction is chromatographed over a column of alumina (25 g of alumina per gram of product), eluting by the ethyl acetate-pentane (15-85) vol/vol mixture.

The first diastereoisomer is firstly obtained: 5(e)-tertiobutyl 3(e)-(2-diisopropylamino ethyl) 3(a)-(2-pyridyl) 2,6-(piperidinedione (SR 41494); weight: 8.7 g, m.p. 101°-102° C. (hexane). Then, after a mixture of the two isomers (2.7 g), the second pure diastereoisomer is isolated: 5(e)-tertiobutyl 3(e)-(2-diisopropylamino ethyl) 3(e)-(2-pyridyl) 2,6-piperidine dione (SR 41584); weight: 5.1 g, m.p. 102°-103° C. (hexane).

EXAMPLE 5

4,4-dimethyl 3-(2-diisopropylamino ethyl) 3-(2-pyridyl) 2,6-piperidinedione (SR 41694)

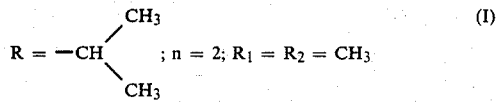

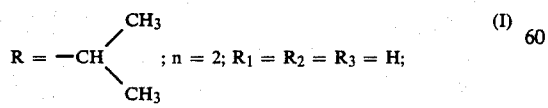

$R_3 = R_4 = R_5 = H$ (a) 2-(2-diisopropylamino ethyl) 3,3-dimethyl 2-(2-pyridyl) pentane-dinitrile The mixture of 4.7 g of sodium amide and 400 ml of liquid ammonia is cooled to −40° C., then the solution of 24.5 g of 4-diisopropylamino 2-(2-pyridyl) butane nitrile (Example 1a) in 30 ml of anhydrous ether is added, the temperature being maintained between −40° C. and −33° C. The mixture is stirred for 15 mins. at this temperature then the solution of 9 g of 3,3-dimethyl acrylonitrile in 40 ml of ether is added, still at the same temperature. The temperature is allowed to rise slowly up to ambient temperature (duration: about 5 hrs.). 200 ml of ether are added then water is added drop by drop. The ethereal phase is separated and the aqueous phase is re-extracted with ether. The ethereal extracts are collected and dried over sodium sulfate. The solvent is evaporated to dryness and the residue is chromatographed over a column of alumina with the eluting ethyl acetate-pentane (2.5-100) vol/vol mixture.

The products which did not react are eliminated at the head, then 12.5 g of the expected product are obtained, used as such for cyclization.

(b) SR 41694

Cyclization is carried out by sulfuric acid as indicated in Example 3(b). The expected product is obtained in the form of colourless crystals; m.p. 105°-106° C. (cyclohexane-hexane).

EXAMPLE 6

4-(2-diisopropylamino ethyl) 4-(2-pyridyl) 1,3-decahydroisoquinoline dione (SR 42420)

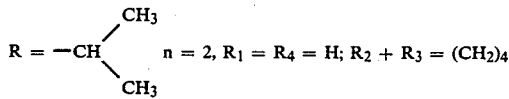

(a) 2-(2-cyano cyclohexyl) 4-diisopropylamino 2-(2-pyridyl) butyronitrile

To the solution of 36.75 g of 4-diisopropylamino 2-(2-pyridyl) butyronitrile (Example 1a) in 300 ml of tetrahydrofuran are added at ambient temperature 71.7 g of Triton B then 15.9 g of 1-cyclohexene carbonitrile dissolved in 100 ml of tetrahydrofuran. The mixture is left for one night with stirring at ambient temperature (about 20° C.), then the solvent is evaporated to dryness. The residue is taken up in water and extracted 3 times with ether. The solvent is evaporated and the residue is chromatographed over a column of alumina. By eluting with a pentane-ethyl acetate (80-20) vol/vol mixture, 20 g of the expected product are obtained, used as such for cyclization.

(b) SR 42420

The mixture of 20 g of the product obtained hereinbefore and 200 ml of concentrated sulfuric acid (d=1.83) is heated to 100° C. for 1 hour. After cooling, it is poured over ice then rendered alkaline with a 40% sodium hydroxide solution, cooling so that the temperature of the mixutre does not exceed 30° C. It is extracted three times with ethyl acetate and the organic extracts are dried over sodium sulfate. The solvent is evaporated to dryness and the residue is chromatographed over a column of alumina. By eluting with the pentane-ethyl acetate (90-10) vol/vol mixture, the expected product is obtained (4.3 g); m.p.: 159°-160° C. (isopropyl ether).

EXAMPLE 7

3-(2-diisopropylamino ethyl) 5,5-dimethyl 3-(2-pyridyl) 2,6-piperidinedione dihydrochloride (SR 41298)

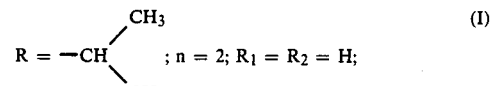

$R_3 = R_4 = CH_3; R_5 = H$ (a) 4-cyano 2,2-dimethyl 4-(2-pyridyl) butene-3-oate of ethyl In a flask fitted with a water separator, 12.8 g of 2-pyridyl acetonitrile, 22 g of 2-formyl 2-methyl propionate of ethyl, 500 ml of benzene, 1 ml of acetic acid and 0.2 ml of piperidine are introduced.

The mixture is taken to reflux until no water separates (about 69 hrs.) then, after cooling, the organic solution is washed with a solution of sodium bicarbonate. The solution is dried over sodium sulfate then the solvent is evaporated to dryness.

The product is used as such for the following step.

(b) 4-cyano-2,2-dimethyl 4-(2-pyridyl)butyrate of ethyl

The product obtained above is dissolved in 600 ml of ethanol and 15 g of palladium on charcoal at 5% are added. Hydrogenation is effected at ambient temperature under 1 atmosphere. The catalyst is filtered and the solvent is evaporated to dryness.

The residue is distilled under high vacuum.
b.p./0.001 mm Hg: 117°-120° C. weight: 20.8 g.

(c) 4-cyano 2,2-dimethyl 4-(2-diisopropylamino ethyl) 4-(2-pyridyl) butyrate of ethyl.

1.4 g of sodium hydride and 20 ml of dimethylformamide are placed in a flask in an atmosphere of nitrogen. The solution of 9.8 g of the compound obtained in (b) in 20 ml of dimethylformamide is added drop by drop. The mixture is left for 1 hour wih stirring at ambient temperature then the solution of 7.2 g of 1-chloro-2-diisopropylamino ethane in 20 ml of dimethylformamide is added and the mixture is left for 2 hours with stirring at ambient temperature.

The solvent is evaporated to dryness and the residue is taken up in ether. The solution is washed with water, dried over sodium sulfate and the solvent is evaporated to dryness.

The product thus obtained is used as such in the following step.

(d) SR 41298

The compound obtained above is dissolved in 130 ml of concentrated sulfuric acid (d=1.83) and the reaction mixture is heated for 1 hour at 100°-110° C. The mixture is poured over ice and the solution is rendered alkaline by addition of an aqueous solution of potassium carbonate. It is extracted with ethyl acetate and the solution is dried over sodium sulfate.

The solvent is evaporated to dryness and the residue is chromatographed over a column of alumina. By firstly eluting with the ethyl acetate-pentane (50-50)

vol/vol mixture, then with pure ethyl acetate, 11.7 g of the expected product are obtained.

Dihydrochloride 10 g of the above base are dissolved in 100 ml of ethanol and 5.8 g of concentrated hydrochloric acid (d=1.18) are added. The mixture is evaporated to dryness and ether is added. The residue crystallizes.

Recrystallization is effected in absolute alcohol. Colourless crystals are obtained (7.3 g); m.p.: 203°–204° C.

The hydrochloride crystallizes with 1 molecule of water.

EXAMPLES 8 to 21

By operating as in Example 7, but by varying the carbonyl derivative used in paragraph (a) and/or the halogen derivative used in paragraph (c), the compounds (I) collected together in Table I hereinafter are obtained in the same manner.

TABLE 1

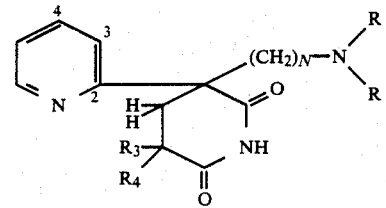

| Example n° | No. of code SR | Position substitution pyridine | $-N\begin{smallmatrix}R\\R\end{smallmatrix}$ | n | $R_3$ | $R_4$ | Base or salt | Melting point °C. (solvent of crystallization) |
|---|---|---|---|---|---|---|---|---|
| 8 | 41338 | 2 | —N[CH(CH₃)₂]₂ | 2 | (CH₂)₄ | | Base | 86–87 (isopropyl ether) |
| 9 | 41612 | 2 | —N[CH₂CH₂CH₃]₂ | 2 | —CH₃ | —CH₃ | Base | 73–74 (hexane) |
| 10 | 41620 | 2 | 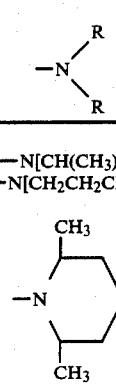 | 2 | —CH₃ | —CH₃ | Base | 153–154 (ethyl acetate) |
| 11 | 41639 | 2 | 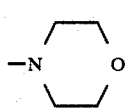 | 2 | —CH₃ | —CH₃ | Base | 163–164 (ethyl acetate) |
| 12 | 41692 | 2 | —N[CH(CH₃)₂]₂ | 2 | —CH₂CH₃ | —CH₂CH₃ | dihydrochloride with 1,5 H₂O | 124–126 (isopropanol) |
| 13 | 41700 | 2 | " | 3 | —CH₃ | —CH₃ | Base | 94–95 (isopropyl ether) |
| 14 | 41720 | 2 | 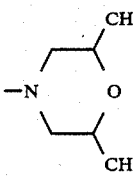 | 2 | —CH₃ | CH₃ | Base | 119–120 (isopropyl ether) |
| 15 | 41770 | 2 | —N—(CH₂CH₃)₂ | 2 | —CH₃ | —CH₃ | Base | 83–85 (hexane) |
| 16 | 41811 | 2 | —N[CH(CH₃)(C₂H₅)]₂ | 2 | —CH₃ | —CH₃ | Base | 65–67 (hexane) |
| 17 | 41821 | 2 | 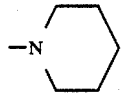 | 2 | —CH₃ | —CH₃ | Base | 136–137 (isopropyl ether) |
| 18 | 42138 | 4 | —N[CH(CH₃)₂]₂ | 2 | —CH₃ | —CH₃ | Base | 132–134 (isopropyl ether) |
| 19 | 42150 | 3 | " | 2 | —CH₃ | —CH₃ | Base | 51–53 (hexane) |
| 20 | 42151 | 2 | 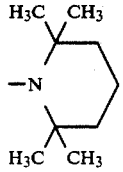 | 2 | —CH₃— | —CH₃ | Base | 198–199 (ethyl acetate) |

TABLE 1-continued

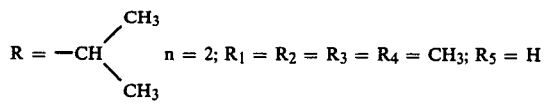

| Example n° | No. of code SR | Position substitution pyridine | −N⟨R,R | n | R₃ | R₄ | Base or salt | Melting point °C. (solvent of crystallization) |
|---|---|---|---|---|---|---|---|---|
| 21 | 42241 | 2 | CH₃ <br> 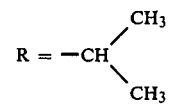 <br> CH₃ | 2 | —CH₃ | —CH₃ | Base | 145–146 (isopropyl ether) |

EXAMPLE 22

3-(2-diisopropylamino ethyl) 3-(2-pyridyl) 4,4,5,5-tetramethyl 2,6-piperidinedione (SR 42436)

$$R = -CH\begin{matrix}CH_3\\CH_3\end{matrix} \quad n = 2; R_1 = R_2 = R_3 = R_4 = CH_3; R_5 = H \quad (I)$$

(a) 4-(2-pyridyl)2,2,3,3-tetramethyl 1,5-pentane dinitrile.

To 68 ml of a solution of 1,6M n butyllithium in hexane cooled to −20° C. there is added, with stirring in an atmosphere of nitrogen, the solution of 11.1 g of diisopropylamine in 100 ml of tetrahydrofuran. The mixture is then cooled to −70° C. and the solution of 6.9 g of isobutyronitrile in 100 ml of tetrahydrofuran is added. After 15 minutes of stirring at −70° C., the solution of 17.4 g of 3-methyl 2-(2-pyridyl) 2-butene nitrile in 100 ml of tetrahydrofuran is added.

After the end of the addition, the temperature is left to rise slowly up to ambient temperature then the solvent is evaporated to dryness. The residue is taken up in water and extracted 3 times with ether. The organic extracts are dried over sodium sulfate and the solvent is evaporated. The residue is distilled under reduced pressure and 11.3 g of a red liquid is collected; b.p./1.5 mm Hg: 160°–170° C.

(b) 6-diisopropylamino 4-(2-pyridyl) 4-cyano 2,2,3,3-tetramethyl hexane nitrile.

In an atmosphere of nitrogen are added 2.4 g of a 55% suspension of sodium hydride in oil in 50 ml of dimethylformamide. The solution of 11.3 g of the dinitrile obtained previously in 50 ml of dimethylformamide is then added drop by drop. The mixture is stirred for 30 minute at ambient temperature, then the solution of 9 g of 1-chloro 2-diisopropylamino ethane in 50 ml of dimethylformamide is added. The mixture is stirred for 4 hours at ambient temperature then the solvent is evaporated in vacuo. The residue is taken up in water and extracted with ethyl acetate. The solution is dried over sodium sulfate and the solvent is evaporated in vacuo. The residue is chromatographed over a column of alumina. By eluting with the pentane-ethyl acetate (90-10) vol/vol mixture, a viscous liquid is obtained (16 g) used as such for cyclization.

(c) SR 42436

16 g of the compound obtained previously and 150 ml of concentrated sulfuric acid (d=1.83) are heated to 100° C. for 1 hour. 300 ml of water are added and taken to reflux for 12 hours. After cooling, the mixture is rendered alkaline by the addition of 40% sodium hydroxide solution by cooling on the outside so as to maintain the temperature of the reaction mixture below 30° C.

The mixture is extracted 3 times with ethyl acetate and the organic extracts are dried over sodium sulfate. The solvent is evaporated and chromatographed over a column of alumina. By eluting with a pentane-ethyl acetate (80-20) vol/vol mixture, a thick liquid is obtained which crystallizes in the presence of isopropyl ether. After recrystallization in isopropyl ether, colourless crystals are obtained (4.1 g). m.p. 89°–90° C.

By operating in the same manner, but by replacing in step (a) the 3-methyl 2-(2-pyridyl) 2-butene nitrile by an equivalent quantity of 2-(2-pyridyl) 2-butene nitrile, the following is obtained in the same manner: 3-(2-diisopropylamino ethyl) 3-(2-pyridyl) 4,5,5-trimethyl 2,6-piperidinedione. Colourless crystals, m.p.: 93°–4° C. (isopropyl ether). (SR 42480).

EXAMPLE 23

3-(2-diisopropylamino ethyl) 3-(2-pyridyl) 5,5-dipropyl 2,6-piperidinedione (SR 42481) CH₃

$$R = -CH\begin{matrix}CH_3\\CH_3\end{matrix}$$

n = 2; R₁ = R₂ = R₅ = H R₃ = R₄ = —CH₂CH₂—CH₃

(a) 2-(-chloro ethyl) 2-propyl pentane nitrile

To the solution (245 ml) of 1,6M n butyllithium in hexane is added, drop by drop in an atmosphere of nitrogen and with stirring, the solution of 28.8 g of diethylamine in 100 ml of anhydrous ether. After 1 hour, the solution of 49.2 g of 2-propyl pentane nitrile in 100 ml of anhydrous ether is added at ambient temperature then, after return to ambient temperature, the solution of 49.1 g of 1-bromo 2-chloro ethane in 700 ml of anhydrous ether is added. The mixture is taken to reflux for 15 hours then, whilst cooling the reaction mixture in an ice bath, water is added. The organic phase is separated, washed with water, then with a dilute solution of hydrochloric acid and again with water. It is dried over sodium sulfate and the solvent is evaporated. The residue is distilled and a liquid is obtained; b.p./20 mm Hg: 140°-150° C.

(b) 4-cyano 4-propyl heptane nitrile.

The mixture of 5.62 g of the nitrile obtained in (a), 4.68 g of tetraethylammonium cyanide in 15 ml of acetonitrile, is heated to 50° C. for 16 hours.

The solvent is evaporated to dryness and the residue is taken up in ether. The solution is filtered, the solvent evaporated and the residue distilled. A yellow liquid is obtained (29 g). b.p./20 mm Hg: 160°-170° C.

(c) 4-cyano 4-propyl 2-(2-pyridyl) heptane nitrile.

To 38 ml of a 1.6M solution of n butyllithium in hexane cooled to −10° C. there is added, in an atmosphere of nitrogen, the solution of 6.3 g of diisopropylamine in 100 ml of dry tetrahydrofuran. The solution of 10 g of the compound obtained in (b) in 100 ml of anhydrous tetrahydrofuran is then added at a temperature of between −20° and −10° C. After 15 minutes' stirring, the solution of 9.1 g 2-bromo pyridine in 100 ml of anhydrous tetrahydrofuran is added at −20° C. The temperature of the mixture is then allowed to rise slowly up to ambient temperature then the solvent is evaporated. The residue is taken up in water and extracted 3 times with ether. The organic solution is dried over sodium sulfate and the solvent is evaporated. The residue is chromatographed over a column of alumina. By eluting with the hexane-ethyl acetate (90-10) vol/vol mixture, a thick liquid is obtained (7 g).

(d) 4-cyano 2-(2-diisopropylamino ethyl) 4-propyl 2-(2-pyridyl) heptane nitrile

To the solution of 4 g of the product obtained above in 20 ml of dimethylformamide there is added in a nitrogen atmosphere, 0.8 g of a 55% suspension of sodium amide in oil. The mixture is stirred for 30 minutes at ambient temperature then 2.95 g of 1-chloro 2-diisopropylamino ethane dissolved in 20 ml of dimethylformamide are added.

The mixture is stirred for 2 hours at ambient temperature then the solvent is evaporated in vacuo and the residue is taken up in water. It is extracted with ether and the solution is dried over sodium sulfate. The solvent is evaporated to dryness and the residue is used directly for the following step (6.6 g).

(e) SR 42481

6.6 g of the compound obtained in (d) and 100 ml of concentrated sulfuric acid (d=1.83) are taken to 100° C. for 1 hour. 200 ml of water are then added and the mixture is taken to reflux for 1 hour.

The mixture is rendered alkaline with a 40% sodium hydroxide solution, the temperature of the mixture being maintained below 30° C.

It is extracted with ether, the solution is dried over sodium sulfate then the solvent is evaporated. The residue is chromatographed over a column of alumina. By eluting with the hexane-ethyl acetate (90-10) vol/vol mixture, 5 g of a viscous liquid are obtained.

NMR spectrum recorded at 250 MHz in solution in deuterochloroform. 1H at 8.55 ppm: (Doublet of doublet, $J_1=4$ Hz, $J_2=2$ Hz, $H_6$ pyridine) 1H at 8.08 ppm: (enlarged singlet —NH—) 1H at 7.62 ppm: (triplet of doublet: $J_1=7$ Hz, $J_2=2$ Hz, $H_4$ pyridine) 1H at 7.18 ppm: (multiplet, $H_5$ pyridine) 2H at 2.90 ppm: (septuplet, $J=7$ Hz, $2C\underline{H}(CH_3)_2$ 2H at 2.65 ppm: (multiplet, 1 $H_4$ and 1

4H at 2.00 ppm: (multiplet, 1 $H_4$ and 3

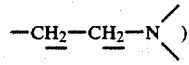

2 H at 1.5 ppm: (multiplet)  
3 H at 1.25 ppm: (multiplet) } 2 chains —CH$_2$CH$_2$—CH$_3$  
5 H at 0.95 ppm: (multiplet)

12H at 0.90 ppm: (doublet $J=7$ Hz, 2 CH(C$\underline{H}_3$)$_2$) 1H at 0.5 ppm: (multiplet, propyl chain) 3H at 0.36 ppm: (triplet, $J=7$ Hz, —CH$_2$CH$_2$—CH$_3$)

EXAMPLE 24

1.5(e)-dimethyl 3(e)-(2-diisopropylamino ethyl) 3(a)-(2-pyridyl) dihydrochloride (SR 41297)

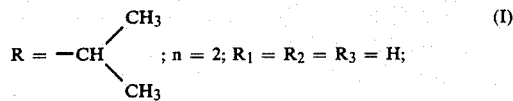

$R_4$ = equatorial CH$_3$; $R_5$ = CH$_3$ 0.7 of sodium hydride are suspended in an atmosphere of nitrogen in 20 ml of dimethylformamide, then a solution of 7.2 g of the compound of Example 1 in 20 ml of dimethylformamide is added drop by drop.

After 1 hour of stirring at ambient temperature, the solution of 3.0 g of methyl iodide in 10 ml of dimethylformamide is added drop by drop. The mixture is stirred again for 1 hour at ambient temperature then the solvent is evaporated to dryness and the residue is taken up in ether. The organic solution is washed with water, dried over sodium sulfate and evaporated to dryness.

The residue is chromatographed over a column of alumina by eluting with the ethyl acetate-pentane (15-85) vol/vol mixture.

An oil is obtained (4.9 g).

Dihydrochloride 4.75 g of the base is dissolved in 50 ml of absolute alcohol and 2.7 g of hydrochloric acid (d=1.18) are added. The mixture is evaporated to dryness and ether is added. Recrystallization takes place in isopropanol.

Colourless crystals are obtained (5 g); m.p.: 167°–169° C. The dihydrochloride crystallizes with 0.75 molecule of water.

The products of the invention have been studied in pharmacology, particularly with a view to demonstrating their anti-arrhythmic properties.

Protocol

The anti-arrhythmic power of these molecules was assessed on an animal model of ventricular arrhythmia.

Mongrel dogs are anaesthetized then subjected to the positioning, by retrograde catheterism, of a metal turn in the coronary bed. At the same time, a frequency modulator micro-emitter is fixed to the animal's back and connected to two precordial electrodes.

The animal, returned to its cage, then shows a progressive thrombosis of the anterior interventricular artery. A localized, transmural myocardial infarction is thus constituted, generating an abnormal but repetitive electrical activity: ventricular tachycardia.

In this state, 16 to 24 hours after the turn has been positioned, the drugs are administered per os and the telemetered system enables the development of the arrhythmia of the alert dog to be followed in real time.

The systolic, sinusal and pathological complexes are permanently metered by electronic processes. The quality and duration of action of the product may thus be quantified. The animal's behaviour is observed.

Results

A product is considered active if it eliminates at least 60% of the abnormal complexes or if it reestablishes the sinusal rhythm.

The results obtained with various products of the invention, after administration at the dose of 50 mg/kg per os, are shown in Table 2 hereinbelow.

In each case, the number of experiments and the duration of activity of the product in question have been indicated.

These results show that the products according to the invention are endowed with considerable activity on arrhythmia with a prolonged duration of action in certain of them.

Furthermore, products (I) are relatively non-toxic and in particular no sign of toxicity has been demonstrated at doses where they are active on arrhythmias.

Consequently, products (I) may be used in human therapeutics as protectors of the myocardium for correcting disorders of the ventricular rhythm of ischemic origin.

The products may be presented in the galenic forms corresponding to administrationn by the oral route (tablets, capsules, etc . . . ) and by the parenteral route (injectable ampoules).

The dose necessary for restoring the sinusal rhythm in man is between about 50 and 150 mg by the intravenous route and between 400 and 800 mg by the oral route, per day.

The following galenic preparation may be indicated by way of example:

| Tablets | |
|---|---|
| SR 41298 | 0.200 g |
| Microcrystalline cellulose | 0.140 g |
| Lactose | 0.140 g |
| Magnesium stearate | 0.020 g |

| Tablets -continued | |
|---|---|
| | 0.500 g |

TABLE 2

| Code No. of product | Number of animals | Duration of activity on the ventricular tachycardia |
|---|---|---|
| SR 40976 | 2 | 2 hrs. 45 and 11 hrs. 35 |
| SR 41297 | 1 | 1 hr. 40 |
| SR 41298 | 3 | longer than 24 hrs the three times |
| SR 41299 | 2 | 3 hrs. 20 and 3 hrs. 50 |
| SR 41338 | 2 | 8 hrs. and more than 24 hrs. |
| SR 41411 | 2 | 3 hrs. 10 and 10 hrs. |
| SR 41463 | 2 | longer than 24 hrs. both times |
| SR 41575 | 3 | from 8 hrs. to more than 24 hrs. |
| SR 41584 | 1 | longer than 24 hrs. |
| SR 41612 | 1 | longer than 24 hrs. |
| SR 41620 | 2 | longer than 24 hrs. both times |
| SR 41639 | 1 | 1 hr. 40 |
| SR 41694 | 1 | 1 hr. 50 |
| SR 41700 | 2 | longer than 24 hrs. both times |
| SR 41494 | 1 | 9 hrs. |
| SR 41770 | 1 | 5 hrs. |
| SR 41811 | 1 | 7 hrs. |

What is claimed is:

1. Derivatives of piperidinedione represented by the formula:

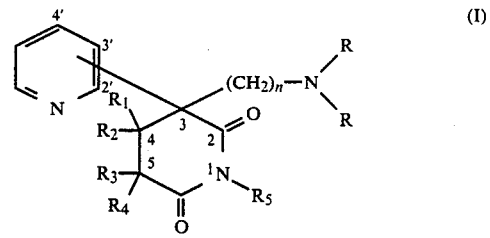

in which:

R represents a straight or branched alkyl group having from 2 to 5 atoms of carbon;

or the group

represents a morpholino or piperidino group possibly substituted by 1 to 4 methyl groups;

n=2 or 3;

$R_1$ and $R_2$ considered independently represent an atom of hydrogen or a lower alkyl group, $R_3$ and $R_4$ considered independently represent hydrogen or a lower alkyl group;

$R_5$ designates hydrogen or a lower alkyl group;

the piperidinedione substitutes the pyridyl group in the 2' position; or salts of said derivatives with pharmaceutically acceptable acids, and wherein at least one of $R_1$, $R_2$, $R_3$ or $R_4$ is other than hydrogen.

2. The derivatives of claim 1 in the form of a diastereoisomer or an optical isomer or a mixture of these isomers.

3. The compound of claim 1 wherein R is isopropyl, n is 2, $R_1$ and $R_2$ are hydrogen, $R_3$ and $R_4$ are methyl, and $R_5$ is hydrogen.

4. The compound of claim 1 wherein R is isopropyl, n is 2, $R_1$, $R_2$ and $R_3$ are hydrogen, $R_4$ is isobutyl and $R_5$ is hydrogen.

5. The compound of claim 1 wherein R is isopropyl, n is 2, $R_1$, $R_2$ and $R_3$ are hydrogen, $R_4$ is ethyl and $R_5$ is hydrogen.

6. The compound of claim 1 wherein R is isopropyl, n is 2, $R_1$, $R_2$ and $R_3$ are hydrogen, $R_4$ is tertiary butyl and $R_5$ is hydrogen.

7. The compound of claim 1 wherein R is propyl, n is 2, $R_1$ and $R_2$ are hydrogen, $R_3$ and $R_4$ are methyl, and $R_5$ is hydrogen.

8. The compound of claim 1 wherein R is isopropyl, n is 3, $R_1$ and $R_2$ are hydrogen, $R_3$ and $R_4$ are ethyl, and $R_5$ is hydrogen.

9. A pharmaceutical composition for protection of the myocardium containing a myocardium protecting amount of a compound according to claim 1 together with a pharmaceutically acceptable carrier.

* * * * *